(12) United States Patent
Kondo

(10) Patent No.: US 9,418,816 B2
(45) Date of Patent: Aug. 16, 2016

(54) X-RAY TUBE AND X-RAY CT DEVICE

(75) Inventor: Gen Kondo, Otawara (JP)

(73) Assignee: TOSHIBA MEDICAL SYSTEMS CORPORATION, Otawara-shi (JP)

( * ) Notice: Subject to any disclaimer, the term of this patent is extended or adjusted under 35 U.S.C. 154(b) by 218 days.

(21) Appl. No.: 13/979,861

(22) PCT Filed: Jun. 21, 2012

(86) PCT No.: PCT/JP2012/065913
§ 371 (c)(1),
(2), (4) Date: Jul. 16, 2013

(87) PCT Pub. No.: WO2013/002124
PCT Pub. Date: Jan. 3, 2013

(65) Prior Publication Data
US 2013/0294571 A1    Nov. 7, 2013

(30) Foreign Application Priority Data
Jun. 28, 2011    (JP) ................................. 2011-142839

(51) Int. Cl.
*H01J 35/30*      (2006.01)
*H01J 35/24*      (2006.01)
(Continued)

(52) U.S. Cl.
CPC ................. *H01J 35/30* (2013.01); *A61B 6/032* (2013.01); *A61B 6/4021* (2013.01); *H01J 35/24* (2013.01);
(Continued)

(58) Field of Classification Search
CPC ........ A61B 6/032; A61B 6/40; A61B 6/4007; A61B 6/4021; A61B 6/482; A61B 6/54; H05G 1/00; H05G 1/08; H05G 1/26; H05G 1/30; H05G 1/52; H01J 35/00; H01J 35/02; H01J 35/04; H01J 35/06; H01J 35/08; H01J 35/14; H01J 35/24; H01J 35/30
USPC ............ 378/16, 91, 98.9, 114, 115, 119, 121, 378/124, 134, 136, 137, 138, 143, 145, 204, 378/210
See application file for complete search history.

(56) References Cited

U.S. PATENT DOCUMENTS 3,158,745 A * 11/1964 Stanhope ...................... 378/137
7,792,241 B2    9/2010 Wu et al.
(Continued)

FOREIGN PATENT DOCUMENTS

CN           1479935 A      3/2004
CN      101076218 A     11/2007
(Continued)

OTHER PUBLICATIONS

International Search Report Issued Jul. 24, 2012 in PCT/JP12/065913 Filed Jun. 21, 2012.
(Continued)

*Primary Examiner* — Anastasia Midkiff
(74) *Attorney, Agent, or Firm* — Oblon, McClelland, Maier & Neustadt, L.L.P.

(57) ABSTRACT

Disclosed is an X-ray tube that has a simple configuration and is capable of irradiating multiple different X-rays while switching them at a high rate, as well as an X-ray CT device using the X-ray tube. The X-ray tube comprises first and second electron generators, a deflection means, and a target. The deflection means switches the direction in which first and second electron beams are transmitted between first and second directions. The target comprises first, second, third, and fourth surfaces. The first surface receives a first electron beam transmitted toward the first direction and irradiates a first X-ray toward the irradiation field. The second surface receives a second electron beam transmitted toward the first direction and irradiates a second X-ray toward a direction different from the irradiation field. The third surface receives a first electron beam transmitted toward the second direction and irradiates the first X-ray toward a direction different from the predetermined irradiation field. The fourth surface receives a second electron beam transmitted in the second direction and irradiates the second X-ray toward the irradiation field.

11 Claims, 7 Drawing Sheets

(51) Int. Cl.
*H05G 1/52* (2006.01)
*A61B 6/03* (2006.01)
*A61B 6/00* (2006.01)
*H01J 35/14* (2006.01)
*H01J 35/08* (2006.01)
*H05G 1/58* (2006.01)

(52) U.S. Cl.
CPC ................ *H05G 1/52* (2013.01); *A61B 6/4078* (2013.01); *A61B 6/482* (2013.01); *H01J 35/08* (2013.01); *H01J 35/14* (2013.01); *H01J 2235/068* (2013.01); *H01J 2235/086* (2013.01); *H05G 1/58* (2013.01)

(56) References Cited

U.S. PATENT DOCUMENTS

| | | | |
|---|---|---|---|
| 8,208,600 | B2 | 6/2012 | Tsumuraya et al. |
| 8,520,803 | B2* | 8/2013 | Behling ........................ 378/124 |
| 2002/0037067 | A1 | 3/2002 | Horiuchi |
| 2004/0136499 | A1* | 7/2004 | Holland et al. ............... 378/119 |
| 2010/0046712 | A1* | 2/2010 | Behling ........................ 378/124 |
| 2010/0074392 | A1* | 3/2010 | Behling et al. ................... 378/4 |
| 2012/0163530 | A1* | 6/2012 | Sainath ................ A61B 6/027 378/5 |

FOREIGN PATENT DOCUMENTS

| | | |
|---|---|---|
| CN | 101395691 A | 3/2009 |
| CN | 101726502 A | 6/2010 |
| CN | 101772324 A | 7/2010 |
| CN | 101897595 A | 12/2010 |
| DE | 10 2009 004 186 A1 | 1/2010 |
| JP | 2003-290207 | 10/2003 |
| JP | 2008-168039 | 7/2008 |
| JP | 2010 027340 | 2/2010 |
| JP | 2010 103111 | 5/2010 |
| WO | 2009 011422 | 1/2009 |
| WO | WO 2010/018502 A1 | 2/2010 |
| WO | WO 2011/018729 A1 | 2/2011 |

OTHER PUBLICATIONS

Office Action issued Apr. 28, 2015 in Chinese Patent Application No. 201280012576.9.

* cited by examiner

X-RAY TUBE AND X-RAY CT DEVICE

TECHNICAL FIELD

The present invention is related to an X-ray tube device used in an X-ray CT device.

BACKGROUND ART

An X-ray computer tomographic device (hereinafter referred to as "X-ray CT device") irradiates X-rays toward a subject and also detects the X-rays that have passed through the subject. As a result, projection data composed of the X-ray absorption coefficient inside the subject is obtained.

Among X-ray CT devices, there are multi-tube X-ray CT devices with multiple X-ray tubes (i.e., X-ray tube devices). Such X-ray devices are capable of generating two different X-ray images with a single scan by exposing two X-rays with different energies in alternation. However, a multi-tube X-ray CT device requires in which multiple X-ray tubes is included, and as a result, the device scale increases and the manufacturing cost also increases.

PRIOR ART DOCUMENTS

Patent Documents

[Patent Document 1] Japanese published unexamined application 2010-27340

SUMMARY OF THE INVENTION

Problems to be Resolved by the Invention

The objective of the embodiments of the present invention is to provide an X-ray tube that has a simple configuration and is able to irradiate multiple X-rays with different energies while switching between them at a high rate, as well as an X-ray CT device using this X-ray tube.

Means of Solving the Problems

To achieve the above objective, the first mode of the present invention is an X-ray tube comprising a first electron generator, a second electron generator, a deflection means, and a target. The first electron generator emits a first electron beam. The second electron generator emits a second electron beam that has a different energy from the first electron beam. The deflection means is configured to be able to switch the direction in which the first electron beam and the second electron beam are transmitted to at least either a first direction or a second direction that is different from the first direction. The target comprises a first surface, a second surface, a third surface and a fourth surface. The first surface receives a first electron beam transmitted toward the first direction and irradiates a first X-ray toward a predetermined irradiation field. The second surface receives a second electron beam transmitted toward the first direction and irradiates a second X-ray that is different from the first X-ray toward a direction that is different from the predetermined irradiation field. The third surface receives a first electron beam transmitted toward the second direction and irradiates a first X-ray toward a direction different from the predetermined irradiation field. The fourth surface receives a second electron beam transmitted toward the second direction and irradiates the second x-ray toward the predetermined irradiation field.

The second mode of the present invention is an X-ray CT device comprising an X-ray tube and an X-ray detector. The X-ray tube comprises an irradiation window for irradiating X-rays toward a subject. The X-ray detector detects X-rays irradiated from the X-ray tube. The X-ray tube comprises a first electron generator, a second electron generator, a deflection means, and a target. The first electron generator emits a first electron beam. The second electron generator emits a second electron beam that is different from the first electron beam. The deflection means is configured to be able to switch the direction in which the first electron beam and the second electron beam are transmitted to at least either a first direction or a second direction that is different from the first direction. The target comprises a first surface, a second surface, a third surface and a fourth surface. The first surface receives a first electron beam transmitted toward the first direction and irradiates a first X-ray toward the subject via the irradiation window. The second surface receives a second electron beam transmitted toward the first direction and irradiates a second X-ray that is different from the first X-ray toward a direction different from the irradiation window. The third surface receives a first electron beam transmitted toward the second direction and irradiates the first X-ray toward a direction different from the irradiation window. The fourth surface receives a second electron beam transmitted toward the second direction and irradiates the second X-ray toward the subject via the irradiation window. In synchronization with the switch performed by the deflection means, the X-ray detector differentiates and detects the first X-rays and the second X-rays by time division.

MODES FOR CARRYING OUT THE INVENTION

Figure 1:
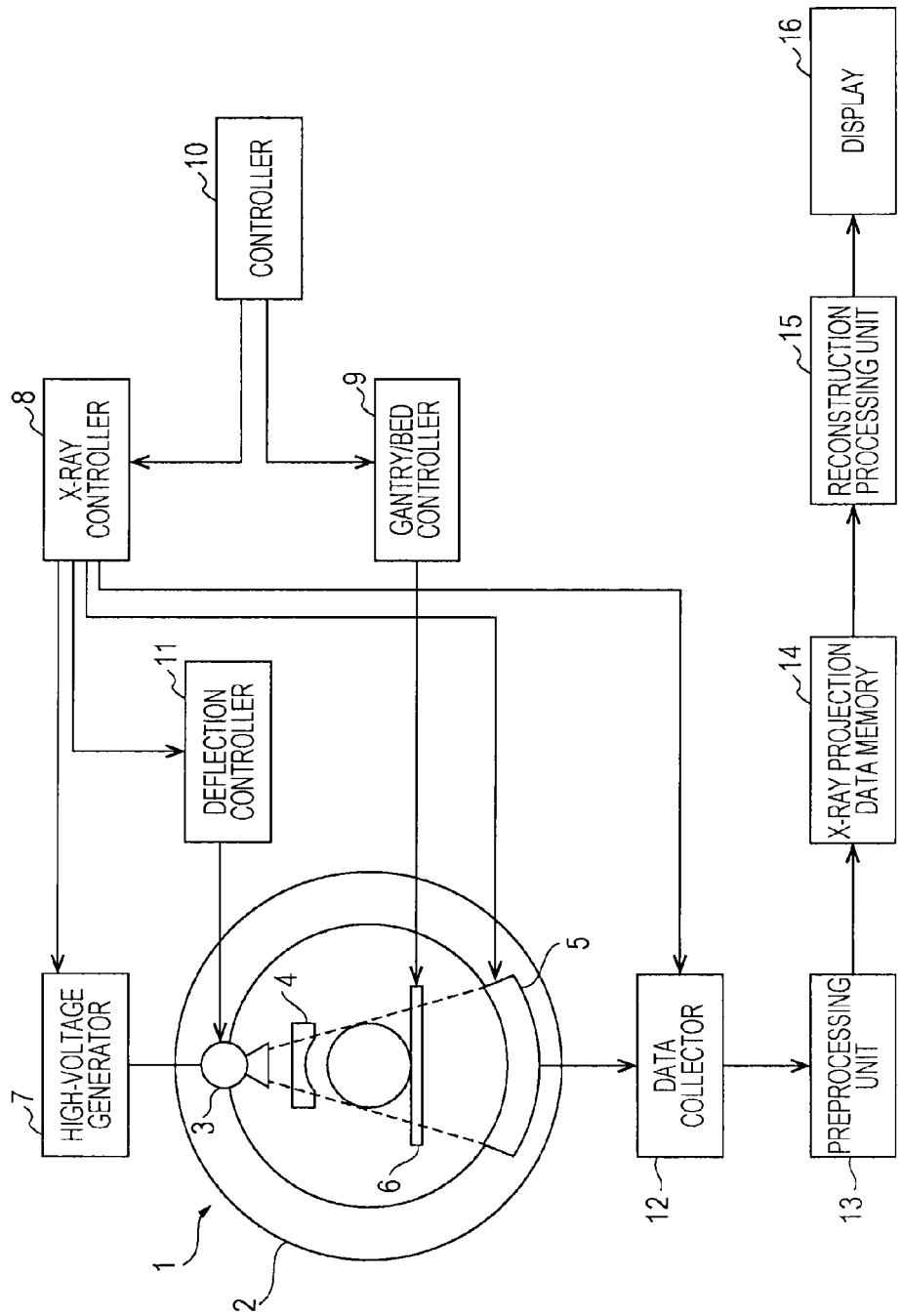
FIG. 1 is a block diagram of an X-ray CT device according to the present embodiment.

The X-ray CT device according to the present invention is described below with reference to FIG. 1. As shown in FIG. 1, the X-ray CT device includes a gantry 1 that houses a rotating ring 2, an X-ray tube 3 that generates conical X-ray beams, and an X-ray filter 4. The gantry 1 has an array-type X-ray detector 5 that includes detecting elements arranged in one or two dimensions.

The X-ray tube 3 and the X-ray detector 5 are arranged on the rotating ring 2 and are positioned on opposing sides across a subject placed on their side on a sliding bed 6. The X-ray detector 5 is configured with multiple detecting elements 5A. The X-ray tube 3 faces the subject via the X-ray filter 4. An X-ray controller 8 generates trigger signals based on the control of a controller 10. Based on the trigger signals, the X-ray controller 8 controls the operations and operational timing of a high-voltage generator 7, a deflection controller 11, the X-ray detector 5 and a data collector 12 based on the control of the controller 10. Upon receiving an instruction from the X-ray controller 8, the high-voltage generator 7 drives the X-ray tube 3. When the output of trigger signals is started, the high-voltage generator 7 applies a high voltage to the X-ray tube 3. As a result, X-rays are irradiated from the X-ray tube 3 toward the subject. A series of operations and the operational timing thereof are described later together with the details of the X-ray controller 8.

Figure 2A:
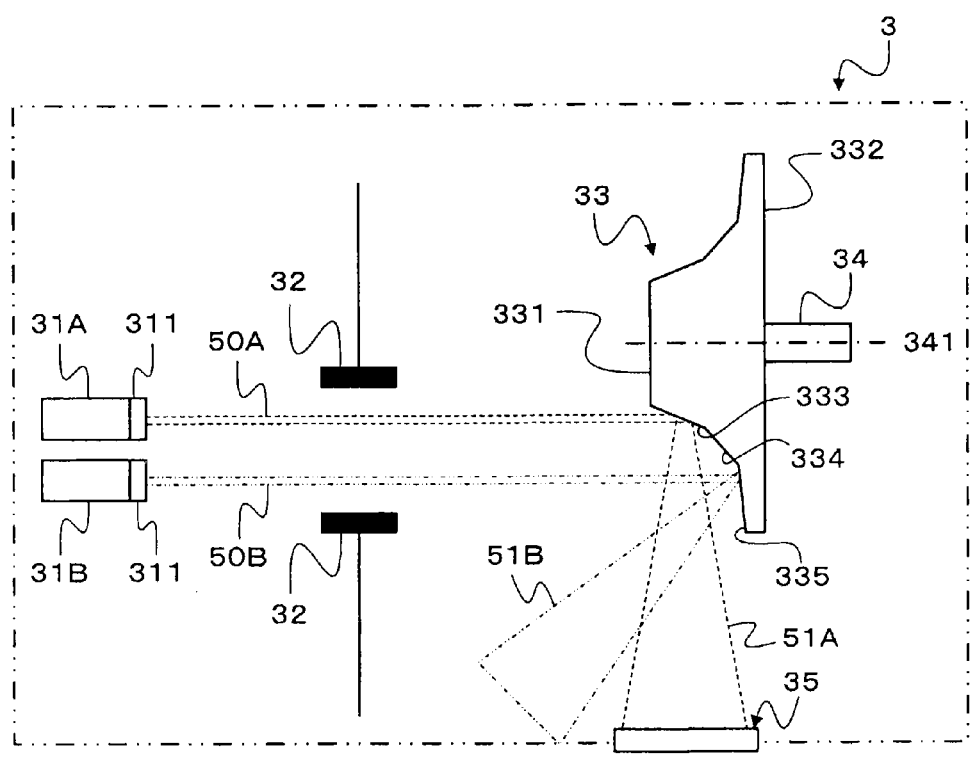
FIG. 2A is a pattern diagram of an X-ray tube according to the present embodiment.
Figure 2B:
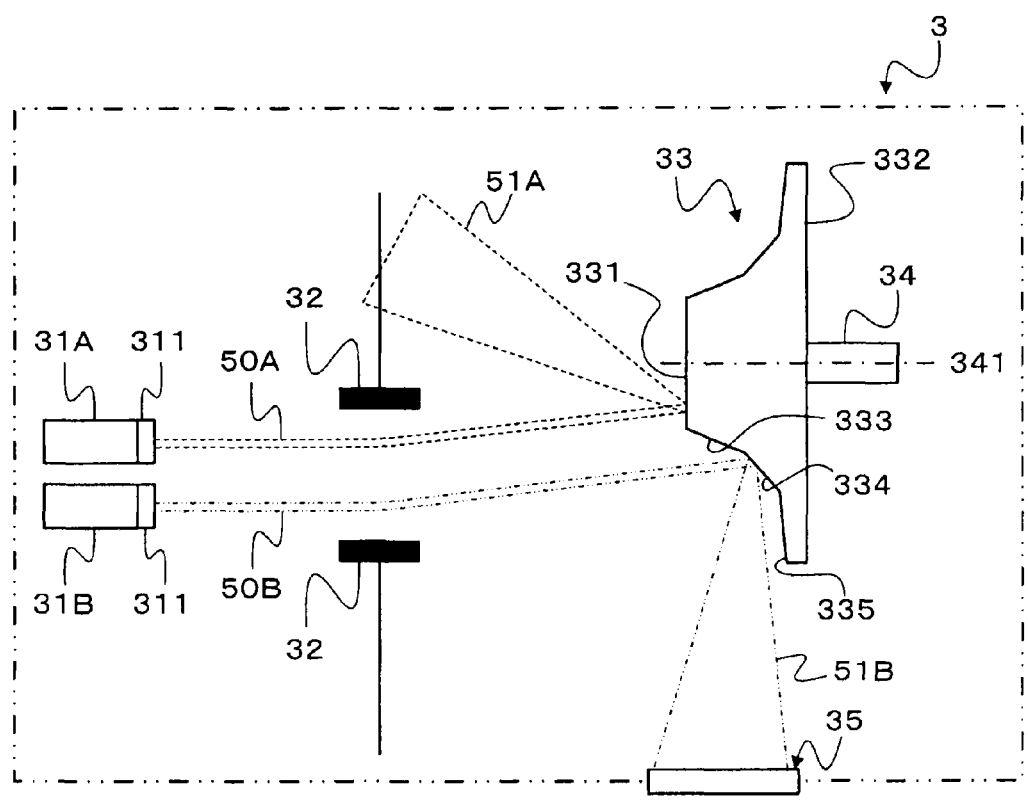
FIG. 2B is a pattern diagram of an X-ray tube according to the present embodiment.

The X-ray tube 3 according to the present embodiment is configured to be able to irradiate two X-rays with different energies while switching them alternately. The following is a description of the specific configuration of the X-ray tube 3 referring to FIG. 2A and FIG. 2B. FIG. 2A and FIG. 2B are pattern diagrams showing schematic configurations of the X-ray tube 3 according to the present embodiment.

As shown in FIG. 2A, the X-ray tube 3 includes electron generators 31A and 31B, a deflection electrode 32, a target 33, a drive member 34, and an irradiation window 35. The target 33 includes a small-diameter surface 331, a large-diameter surface 332, a first side surface 333, a second side surface 334, and a third side surface 335.

The electron generators 31A and 31B each have a filament 311. The high voltage generated by the high-voltage generator 7 is applied between the filament 311 and the target 33. As a result, electrons shoot out from the filament 311, and these electrons collide against the target 33 (anode). As a result, X-rays are irradiated from the target 33. As shown in FIG. 2A, the electron beam 50A generated and emitted from the filament 311 of the electron generator 31A advances linearly toward a first side surface 333. At this time, the electron beam 50A passes through between the deflection electrode 32. Similarly, the electron beam 50B generated and emitted from the filament 311 of the electron generator 31B advances linearly toward a third side surface 335. At this time, the electron beam 50B passes through between the deflection electrode 32.

The deflection electrode 32 is composed of two metal plates, which are arranged so that the electron beams 50A and SOB pass through between the two metal layers. When a voltage is applied to the deflection electrode 32, one of the metal plates of the deflection electrode 32 becomes an anode and the other becomes a cathode. In the present embodiment, the electrode 32 in the upper side in FIG. 2A becomes the anode and electrode 32 in the lower side. In the following description, the state in which a voltage is applied to the deflection electrode 32 is referred to as on, and the state in which no voltage is applied to the deflection electrode 32 is referred to as off.

FIG. 2A shows the state in which the deflection electrode 32 is off. As shown in FIG. 2A, when the deflection electrode 32 is off, the electron beams 50A and 50B advance linearly without being deflected. At this time, the electron beam 50A advances in the direction of the first side surface 333 and the electron beam 50B advances in the direction of the third side surface 335.

Here, reference is made to FIG. 2B. FIG. 2B shows the state in which the deflection electrode 32 is on. As shown in FIG. 2B, when the deflection electrode 32 is on, the electron beams 50A and 50B are refracted. At this time, the electron beam 50A advances in the direction of the small-diameter surface 331 and the electron beam 50B advances in the direction of the second side surface 334.

In this way, by switching on and off, the deflection electrode 32 causes the electron beams 50A and 50B emitted from the electron generators 31A and 31B and each filament 311 to switch and advance in two different directions. The deflection electrode 32 corresponds to the "deflection means". Here, in the present embodiment, the electron beams are deflected by applying a voltage to the deflection electrode 32 to generate an electrical field, but other methods may be used. For example, a coil may be arranged to the side of the direction of advancement of the electron beam and the electron beams may be deflected by applying a magnetic field to the coil. Alternatively, both an electrical field and a magnetic field may be used.

The switching on and off of the deflection electrode 32 is performed by receiving control signals from the deflection controller 11 described below (refer to FIG. 1). When the deflection electrode 32 becomes on, the deflection electrode 32 causes the electron beams 50A and 50B passing through between the electrodes to refract toward the anode. As a result, the direction of advancement of the electron beams 50A and 50B is changed. As a result of this change in the direction of advancement, the electron beam 50A advances in the direction of the small-diameter surface 331 and the electron beam 50B advances in the direction of the second side surface 334. The smaller the refraction angle of the electron beams 50A and 50B, the responsiveness of the switching on and off improves. The greater the refraction angle, the direction of advancement of the electron beams 50A and 50B after reflection becomes easy to control. Therefore, the refraction angle of the electron beams 50A and 50B and the installation positions of the small-diameter surface 331 and the first through third side surfaces 333 through 335 are determined by considering the responsiveness of the switching on and off as well as the ease of control of the direction of the X-rays irradiated from the target 33.

The irradiation window 35 is provided to output X-rays irradiated from the target 33 to outside the X-ray tube 3. With the exception of the irradiation window 35, the inner wall of the X-ray tube 3 is formed with a material that absorbs X-rays. As a result, X-rays irradiated from the target 33 are output toward outside the X-ray tube 3 via the irradiation window 35.

The target 33 is also referred to as an "anode" and is formed with copper, aluminum or tungsten, etc. The target 33 is an axial body that rotates about a central axis 341 and has a rotatable form. The target 33 is configured by including the small-diameter surface 331 and the large-diameter surface 332. The small-diameter surface 331 and the large-diameter surface 332 are set so that the central axis 341 perpendicularly passes through the center of each surface. The first side surface 333, the second side surface 334 and the third side surface 335 are provided consecutively in this sequence so that the axis diameter continually increases from the small-diameter surface 331 to the large-diameter surface 332. At this time, the first side surface 333, the second side surface 334, and the third side surface 335 are provided so that the angle formed by each surface relative to the central axis 341 increases in order of the first side surface 333, the second side surface 334 and the third side surface 335.

As shown in FIG. 2A, the target 33 is arranged so that the direction in which the electron beams 50A and 50B emitted from each filament 311 of the electron generators 31A and 31B is parallel with the central axis 341.

The target 33 is arranged so that when the deflection electrode 32 is off, the electron beam 50A advancing linearly hits the first side surface 333 and the electron beam 50B advancing linearly hits the third side surface 335. When the electron beam 50A hits the target 33, X-rays 51A are generated. The first side surface 333 is formed with a predetermined angle against the central axis 341 so that the X-rays 51A generated from the first side surface 333 are irradiated toward the irradiation window 35. When the electron beam 50B hits the target 33, X-rays 51B are generated. The third side surface 335 is formed with a predetermined angle against the central axis 341 so that the X-rays 51B generated from the third side surface 335 are irradiated toward a direction different from the position where the irradiation window 35 is provided. The target 33 corresponds to the "X-ray generator". The first side surface 333 corresponds to the "first surface", and the third side surface 335 corresponds to the "second surface".

The target 33 is arranged so that when the deflection electrode 32 is on, the electron beam 50A deflected by the deflection electrode 32 hits the small-diameter surface 331 and the electron beam 50B deflected by the deflection electrode 32 hits the second side surface 334. The small-diameter surface 331 is formed in a manner wherein the X-rays 51A generated from the small-diameter surface 331 are irradiated toward a direction different from the position where the irradiation window 35 is provided. The second side surface 334 is formed with a predetermined angle against the central axis 341 so that the X-rays 51B generated from the second side surface 334 are irradiated toward the irradiation window 35. The small-diameter surface 331 corresponds to the "third surface" and the second side surface 334 corresponds to the "fourth surface".

The drive member 34 rotates the target 33 about the central axis 341. When the electron beams 50A and 50B are continuously irradiated to a specific location, the target 33 melts due to the high temperature. Therefore, by rotating the target 33 using the drive member 34, the position where the electron beams 50A and 50B are irradiated is continuously changed and this prevents the situation in which the electron beams 50A and 50B are irradiated on only a specific location on the target 33 in each case.

The electron beam 50A enters the first side surface 333 at a smaller angle than the incident angle of the electron beam 50B relative to the second side surface 334. That is, the area of the part of the first side surface 333 receiving the electron beam 50A is greater than the area of the part of the second side surface 334 receiving the electron beam 50B. Therefore, by using the electron beam 50A as the electron beam with high energy from among the electron beams 50A and 50B, it is possible to reduce temperature increases in the target 33. The energy of an electron beam is calculated by using the amount of heat based on either one or both of the voltage applied to the filament 311 and the voltage between the filament 311 and the target 33 as well as the irradiation time of the electron beam.

The X-rays 51A and 51B that are irradiated in directions different from the position where the irradiation window 35 is provided are not used for imaging. Therefore, the small-diameter surface 331 and the third side surface 335 do not necessarily have to always generate X-rays meeting predetermined conditions for imaging. Therefore, for the small-diameter surface 331 and the third side surface 335, materials other than the copper, aluminum or tungsten described above may be used. For example, for the small-diameter surface 331 and the third side surface 335, materials with greater heat resistance than these materials may be used. Moreover, a cooling part that actively cools the target 33 when the electron beams 50A and 50B are not irradiated may be provided. In this case, to increase the cooling efficiency, materials with high thermal conductivity may be used for the small-diameter surface 331 and the third side surface 335.

As described above, the target 33 comprises the small-diameter surface 331 and the first through third side surfaces 333 to 335. As a result, when the deflection electrode 32 is on, the X-rays 51A generated from the first side surface 333 are irradiated from the irradiation window 35 to outside the X-ray tube 3 (i.e., toward the subject). When the deflection electrode 32 is off, the X-rays 51B generated from the second side surface 334 are irradiated from the irradiation window 35 to outside the X-ray tube 3. In this way, it is possible to switch the irradiation of the X-rays 51A and 51B at a high speed by switching the deflection electrode 32 on and off. The X-rays 51A generated from the small-diameter surface 331 and the X-rays 51B generated from the third side surface 335 hit the inner wall of the X-ray tube 3 and are absorbed. Consequently, when one of either the X-rays 51A or 51B are irradiated from the irradiation window 35 to outside the X-ray tube 3, it is possible to block the outward irradiation of the other X-rays from the X-ray tube 3.

The deflection controller 11 receives trigger signals from the X-ray controller 8. In synchronization with the trigger signals, the deflection controller 11 applies a voltage to the deflection electrode 32 of the X-ray tube 3. As a result, the deflection electrode 32 is switched on and off. The timing of this switch is described later together with the details of the X-ray controller 8.

The gantry/bed controller 9 synchronously controls the rotation of the rotating ring 2 of the gantry 1 and the sliding of the sliding bed 6. The controller 10 is configured as the control center of the entire system and controls the X-ray controller 8, the gantry/bed controller 9 and the sliding bed 6, and when X-rays are irradiated from the X-ray tube 3, the rotating ring 2 is rotated through a desired route around the subject.

Figure 3:
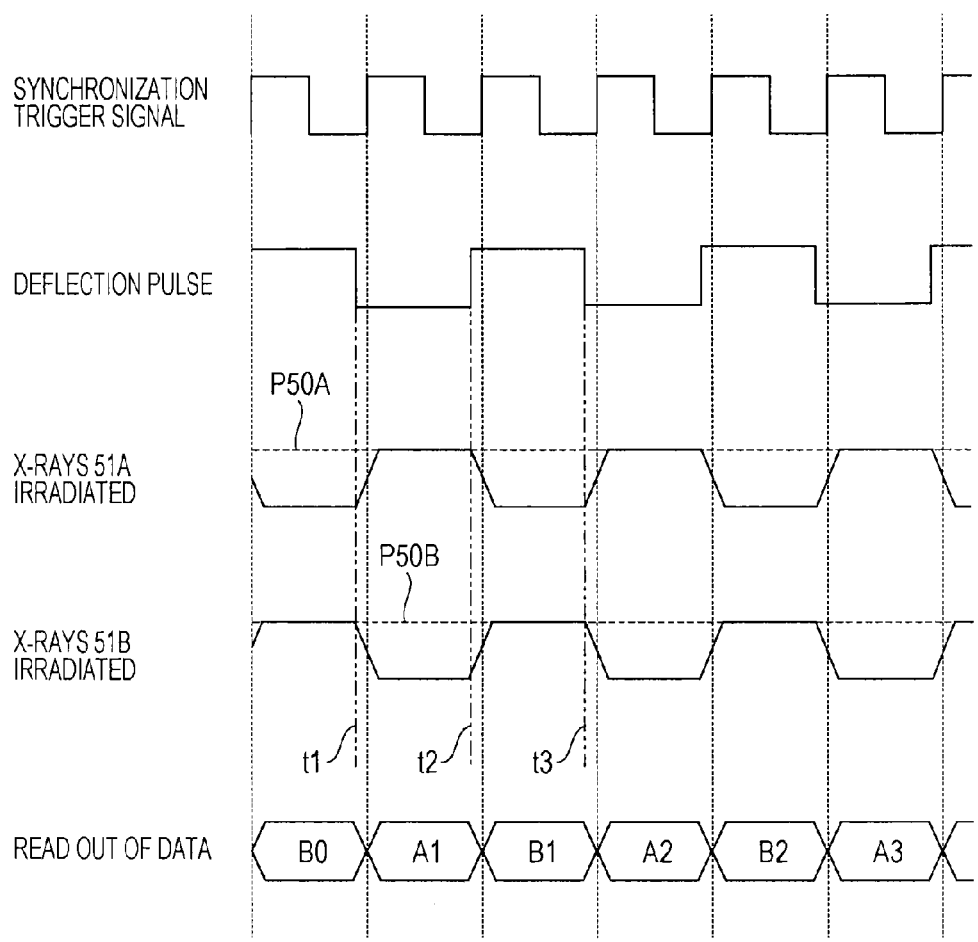
FIG. 3 is an explanatory diagram of the control timing of the X-ray CT device according to the present embodiment.

The X-ray controller 8 controls the operations and operational timing of the high-voltage generator 7, the deflection controller 11, the X-ray detector 5, and the data collector 12. The following is a description of the X-ray controller 8 together with the operational timings of the high-voltage generator 7, the deflection controller 11 and the X-ray detector 5 as well as the operations of the data collector 12 according to each timing, with reference to FIG. 3. FIG. 3 is an explanatory diagram of the control timing of the X-ray CT device.

The X-ray controller 8 first receives, from the controller 10, operating conditions for the X-ray CT device input by the operator. The operating conditions include information indicating tube voltage and irradiation timing (i.e., timing for switching between the X-rays 51A and 51B) as irradiation conditions for the X-rays 51A and X-rays 51B. The X-ray controller 8 outputs the information indicating tube voltage received from the controller 10 to the high-voltage generator 7. The high-voltage generator 7 determines the applied voltage for outputting the electron beams 50A and 50B based on the information.

Next, The X-ray controller 8 generates synchronization trigger signals as shown in FIG. 3 based on the information indicating the timing for switching between the X-rays 51A and 51B. The X-ray controller 8 outputs the generated trigger signals to the high-voltage generator 7, the deflection controller 11, the X-ray detector 5 and the data collector 12. The X-ray controller 8 notifies the deflection controller 11 and the data collector 12 of the timing for switching between the X-rays 51A and 51B (i.e., at which timing to switch the synchronization trigger signals).

When the output of the synchronization trigger signals from the X-ray controller 8 is started, the high-voltage generator 7 applies a voltage between each filament 311 of the electron generator 31A and 31B and the target 33. As a result, the electron beams 50A and 50B are output from the electron generators 31A and 31B, respectively. The output P50A in FIG. 3 indicates the energy of the electron beam 50A output from the electron generator 31A. The output P50B indicates the energy of the electron beam 50B output from the electron generator 31B.

The deflection controller 11 receives the synchronization trigger signals and the timing for switching between the X-rays 51A and 51B from the X-ray controller 8. The deflection controller 11 generates the deflection pulse shown in FIG. 3 in synchronization with the synchronization trigger signals based on the timing for switching between the X-rays 51A and 51B. The deflection controller 11 outputs the generated deflection pulse to the deflection electrode 32 of the X-ray tube 3. Based on this deflection pulse, the deflection electrode 32 is switched on and off. Thus, the X-rays irradiated from the irradiation window 35 of the X-ray tube 3 are switched between the X-rays 51A and 51B in correspondence to the switching between on and off. Specific operational timings are described below with reference to FIG. 3.

For example, as shown in FIG. 3, between the times t1 to t2, no deflection pulse is supplied from the deflection controller 11 to the deflection electrode 32. Thus, the deflection electrode 32 is off. In this case, the electron beams 50A and 50B advance linearly without being deflected. At this time, the electron beam 50A hits the first side surface 333 and the electron beam 50B hits the third side surface 335. The X-rays 51A generated when the electron beam 50A hits the first side surface 333 are irradiated toward the irradiation window 35. The X-rays 51B generated when the electron beam 50B hits the third side surface 335 are irradiated toward a direction different from the position where the irradiation window 35 is provided. As a result, between the times t1 to t2, the X-rays 51A from the irradiation window 35 are irradiated to outside the X-ray tube 3.

Next, using the timing of time t2, the output of a deflection pulse from the deflection controller 11 to the deflection electrode 32 begins. As a result, the deflection electrode 32 is switched from off to on. Therefore, the electron beams 50A and 50B that were advancing linearly are deflected by the electrical field generated in the deflection electrode 32. At this time, the electron beam 50A hits the small-diameter surface 331 and the electron beam 50B hits the second side surface 334. The X-rays 51A generated when the electron beam 50A hits the small-diameter surface 331 is irradiated in a direction different from the position where the irradiation window 35 is provided. The X-rays 51B generated when the electron beam 50B hits the second side surface 334 is irradiated toward the irradiation window 35. As a result, the deflection pulse is output to the deflection electrode 32. During the period from the times t2 to t3, the X-rays 51B are irradiated from the irradiation window 35 to outside the X-ray tube 3.

At the timing of the time t3, the output of a deflection pulse from the deflection controller 11 to the deflection electrode 32 is stopped. Therefore, the deflection electrode 32 turns off, and the X-rays 51A are irradiated from the irradiation window 35 to outside the X-ray tube 3. In this way, in synchronization with the synchronization trigger signals, the X-rays 51A and the X-rays 51B are irradiated from the X-ray tube 3 while being switched in alternation.

The X-ray detector 5 includes multiple detecting elements 5A. The detecting elements 5A configuring the X-ray detector 5 are able to measure the intensity of the X-rays 51A and 51B irradiated from the X-ray tube 3 regardless of whether the subject is or is not interposed between the X-ray tube 3 and the detecting elements 5A.

Each detecting element 5A includes scintillators and photodiodes (PD). Typically, the scintillators and photodiodes have an equivalent number of elements, and X-rays entering the scintillators are converted into visible light and then converted into electrical signals by the photodiodes. Furthermore, the electrical signals converted by the photodiodes (i.e., the analog output signals) are guided to the data collector 12.

In this way, the irradiated X-rays 51A and X-rays 51B are detected by the X-ray detector 5 that operates in synchronization with the synchronization trigger signals. The X-ray detector 5 converts the detected X-rays 51A and X-rays 51B into electrical signals and outputs them to the data collector 12.

The data collector 12 receives the synchronization trigger signals as well as the timings for switching between the X-rays 51A and 51B from the X-ray controller 8. In synchronization with the synchronization trigger signals, the data collector 12 reads out the signals of each detecting element 5A by time division. The data collector 12 differentiates the signals read out by time division between signals based on the X-rays 51A and signals based on the X-rays 51B based on the notified timings for switching between the X-rays 51A and 51B. This operation is described in detail below with reference to FIG. 3.

As shown in FIG. 3, between the times t1 and t2, because no deflection pulse is output to the deflection electrode 32, the X-rays 51A are output from the irradiation window 35 of the X-ray tube 3. At this time, based on notification from the X-ray controller 8, the data collector 12 recognizes that the X-rays 51A are irradiated. Therefore, the data collector 12 recognizes and processes the signals read out between the times t1 and t2 as signals A1 that are based on the X-rays 51A.

Between the times t2 and t3, a deflection pulse is output to the deflection electrode 32 and the X-rays 51B are irradiated from the irradiation window 35 of the X-ray tube 3. At this time, based on notification from the X-ray controller 8, the data collector 12 recognizes that the X-rays 51B are irradiated. Therefore, the data collector 12 recognizes and processes the signals read out between the times t2 and t3 as signals B1 that are based on the X-rays 51B.

The data collector 12 amplifies each signal read out in synchronization with the synchronization trigger signals and converts each of them into digital data. In the following description, digital data obtained by converting signals based on the X-rays 51A are referred to as "digital data based on the X-rays 51A". Digital data obtained by converting signals based on the X-rays 51B are referred to as "digital data based on the X-rays 51B". The data collector 12 differentiates the digital data based on the X-rays 51A from the digital data based on the X-rays 51B and outputs them to a preprocessing unit 13.

The preprocessing unit 13 differentiates the digital data based on the X-rays 51A from the digital data based on the X-rays 51B and receives them from the data collector 12. The preprocessing unit 13 performs processing such as sensitivity correction on each of these items of digital data to create projection data. The preprocessing unit stores each of more than one projection data into an X-ray projection data memory 14.

The reconstruction processing unit 15 reads out the projection data stored in the X-ray projection data memory 14. The reconstruction processing unit 15 back-projects the projection data that have been read out to generate X-ray image data by using a reconstruction algorithm known as the Feldkamp method, for example. The reconstruction processing unit 15 displays the reconstructed X-ray image data on the display 16.

If it is possible to switch the electron beam irradiated from the irradiation window 35 between the electron beams 50A and 50B by switching the deflection electrode 32 on and off, it is not necessary to ensure that the direction in which the electron beams 50A and 50B are emitted is parallel to the central axis 341. For example, it is possible to emit the electron beams 50A and 50B in different directions that do not to interfere with each other. In this case, it is sufficient to adjust the position and angle of the first side surface 333, the second side surface 334, the third side surface 335, and the small-diameter surface 331 based on the direction of emission of the electron beams 50A and 50B.

Variation

The above descriptions have been of a configuration that switches between and outputs 2 types of X-rays, but a configuration may be used that allows for the output of 3 or more types of X-rays. In this case, the number of electron generators 31A provided is equivalent to the number of types of X-rays to be output. Moreover, by adjusting the shape of the side surfaces of the target 33 and the power of the electrical field generated by the deflection electrode 32, each electron beam is deflected in multiple directions in stages.

Figure 4A:
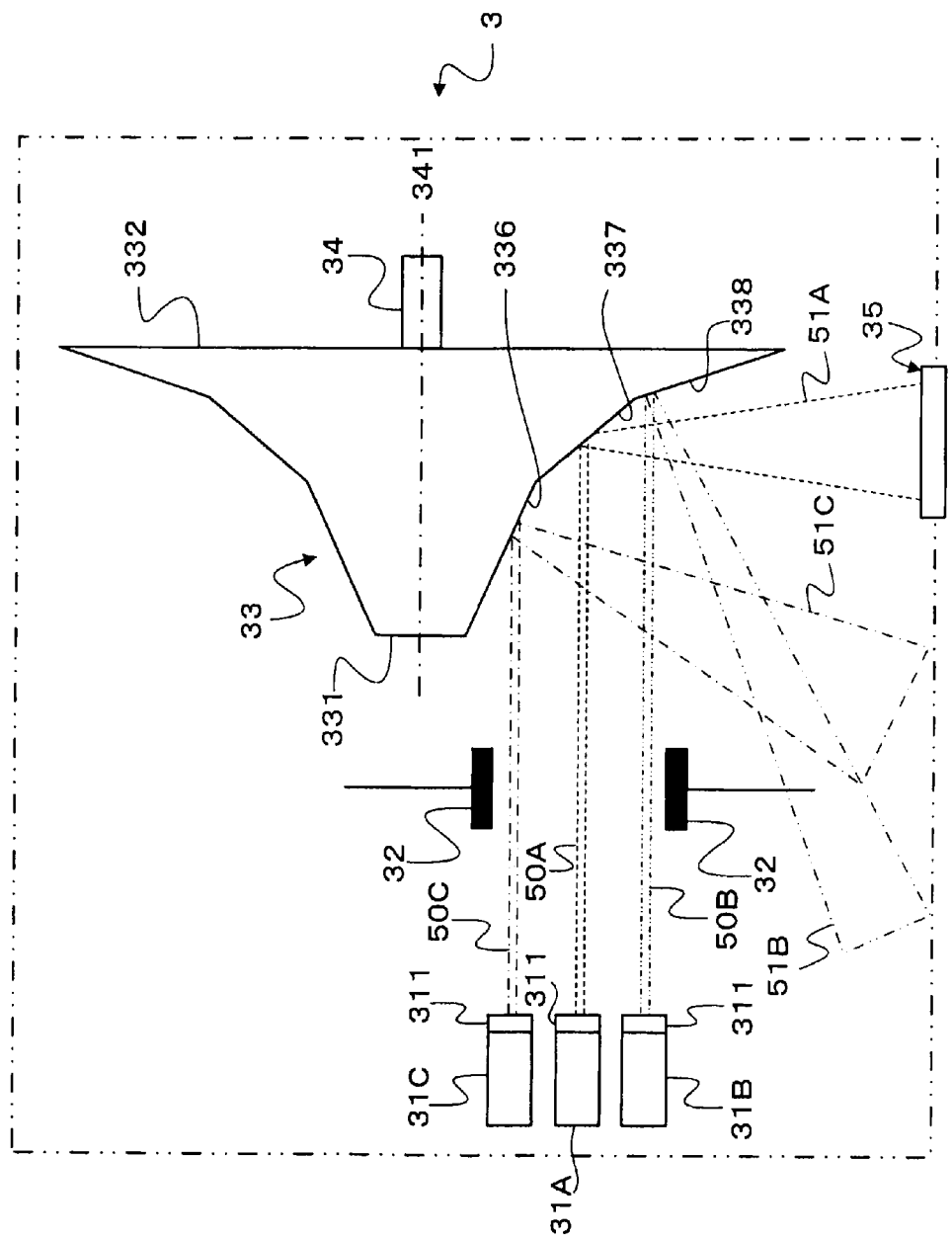
FIG. 4A is a pattern diagram of an X-ray tube according to a variation.
Figure 4B:
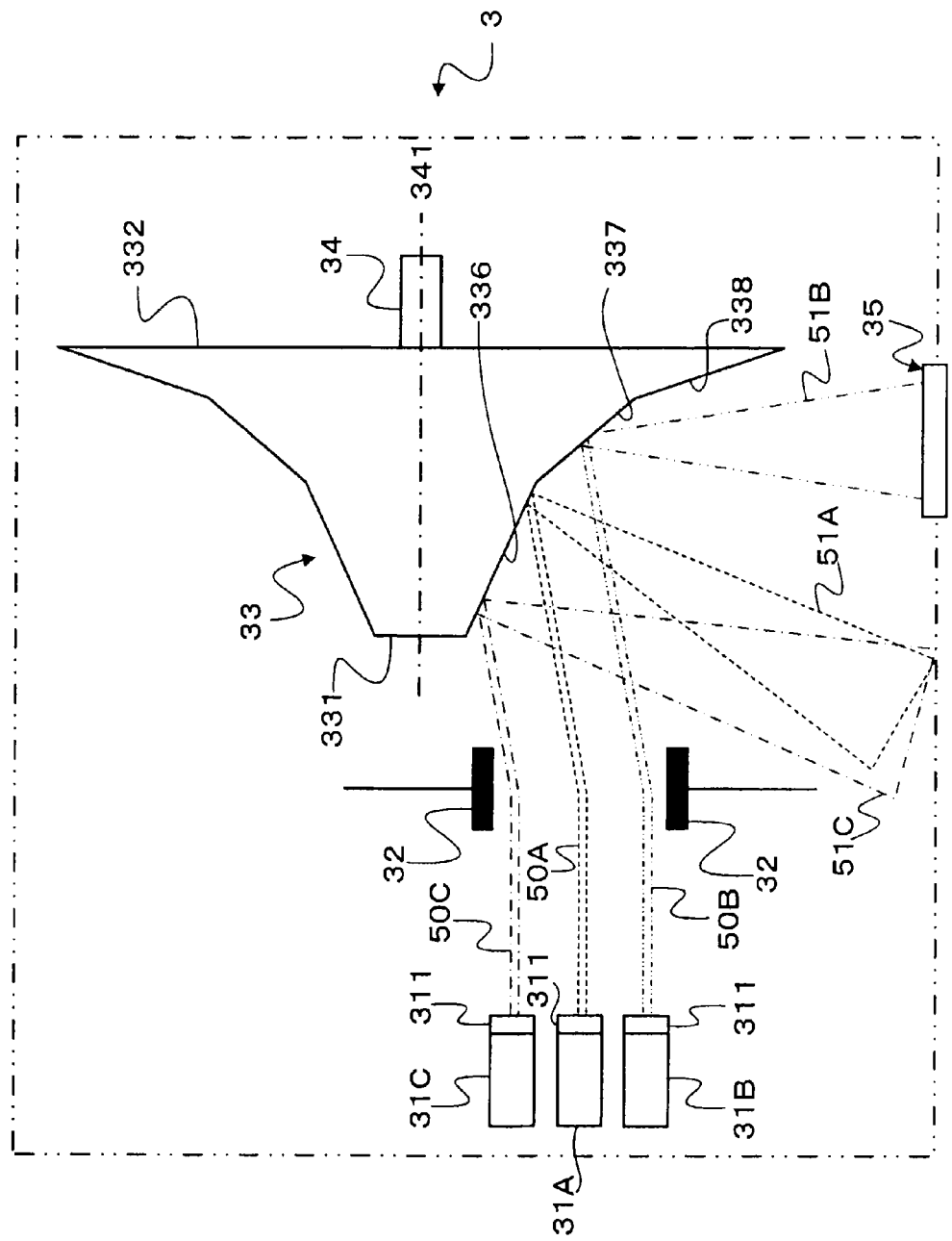
FIG. 4B is a pattern diagram of an X-ray tube according to a variation.
Figure 4C:
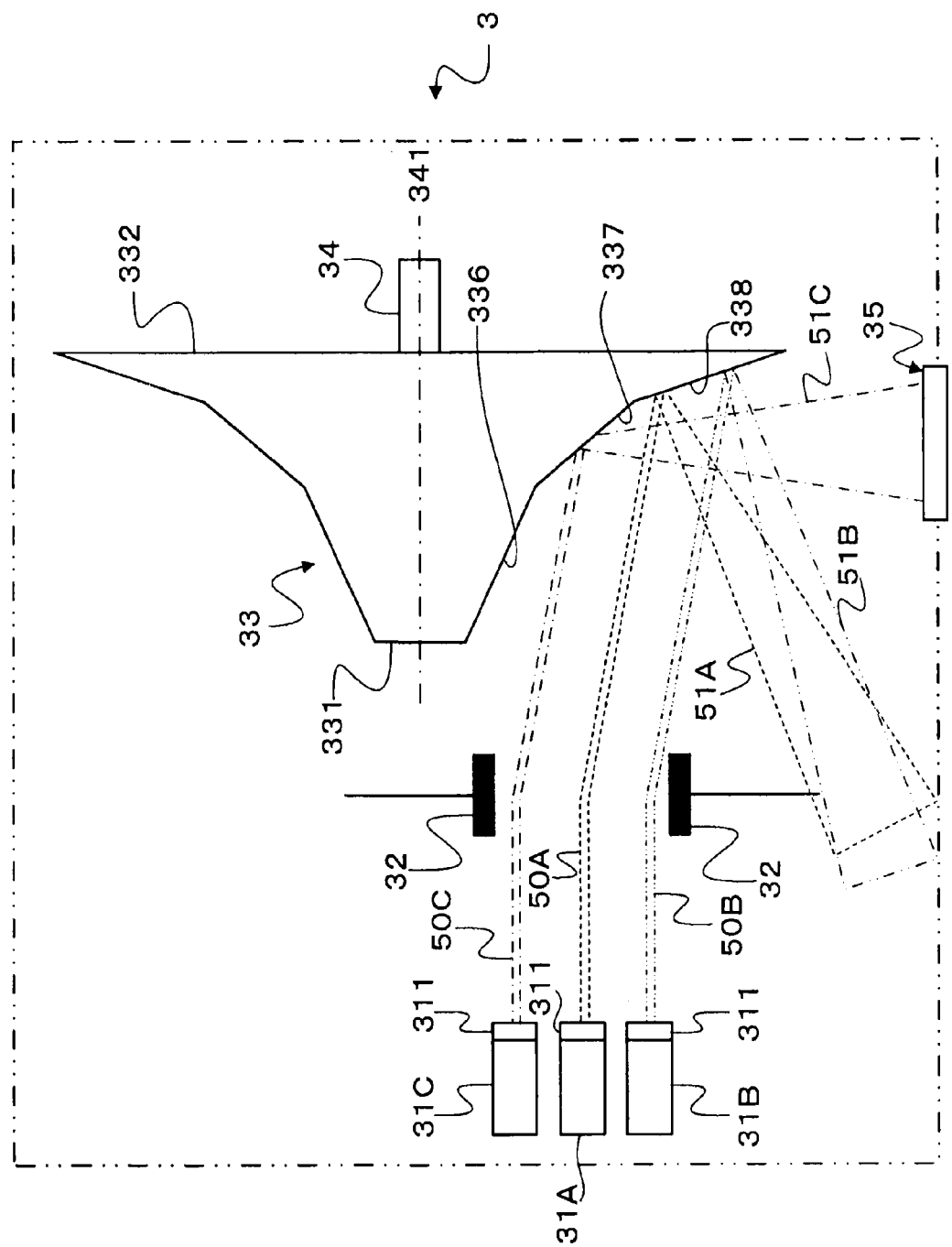
FIG. 4C is a pattern diagram of an X-ray tube according to a variation.

A specific example will now be described with reference to FIG. 4A to FIG. 4C. Here, an example is described in which 3 types of X-rays (electron beam 50A, electron beam 50B, and electron beam 50C) are output using 3 electron generators (electron generator 31A, electron generator 31B and electron generator 31C). FIG. 4A shows the deflection electrode 32 when it is off. FIG. 4B and FIG. 4C show the deflection electrode 32 when it is on. In the cases shown in FIG. 4B and FIG. 4C, the voltages being applied to the deflection electrode 32 are reversed in polarity. With regard to the target 33, in order to make the axis diameter continuously increase from the small-diameter surface 331 to the large-diameter surface 332, the fourth side surface 336, the fifth side surface 337 and the sixth side surface 338 are provided in series in this order.

As shown in FIG. 4A, when the deflection electrode 32 is off, the electron beam 50A, the electron beam 50B and the electron beam 50C advance linearly without being deflected. At this time, the electron beam 50A advances in the direction of the fifth side surface 337, the electron beam 50B advances in the direction of the sixth side surface 338, and the electron beam 50C advances in the direction of the fourth side surface 336.

On the other hand, as shown in FIG. 4B, when a voltage is applied to the deflection electrode 32 (i.e., when it is on), the electron beam 50A, the electron beam 50B and the electron beam 50C are refracted. At this time, the electron beam 50A and the electron beam 50C advance in the direction of the fourth side surface 336 and the electron beam 50B advances in the direction of the fifth side surface 337.

Furthermore, as shown in FIG. 4C, when a voltage with the opposite polarity as that shown in FIG. 4B is applied to the deflection electrode 32 (i.e., when it is on), the electron beam 50A, the electron beam 50B and the electron beam 50C are refracted. At this time, the electron beam 50A and the electron beam 50B advance in the direction of the sixth side surface 338 and the electron beam 50C advances in the direction of the fifth side surface 337.

In the case shown in FIG. 4A, the target 33 is arranged such that the electron beam 50A that has advanced linearly hits the fifth side surface 337, the electron beam 50B that has advanced linearly hits the sixth side surface 338, and the electron beam 50C that has advanced linearly hits the fourth side surface 336. When the electron beam 50A hits the target 33, the X-rays 51A are generated. The fifth side surface 337 is formed with a predetermined angle against the central axis 341 so that the X-rays generated from the fifth side surface 337 (the X-rays 51A in the case shown in FIG. 4A) are irradiated toward the irradiation window 35. When the electron beam 50B hits the target 33, the X-rays 51B are generated. The sixth side surface 338 is formed with a predetermined angle against the central axis 341 so that the X-rays generated from the sixth side surface 338 (the X-rays 51B in the case shown in FIG. 4A) are irradiated in a direction different from the position where the irradiation window 35 is provided. When the electron beam 50C hits the target 33, the X-rays 51C are generated. The fourth side surface 336 is formed with a predetermined angle against the central axis 341 so that the X-rays generated from the fourth side surface 336 (the X-rays 51C in the case shown in FIG. 4A) are irradiated in a direction different from the position where the irradiation window 35 is provided.

In the case shown in FIG. 4B, the target 33 is arranged such that the electron beam 50A and the electron beam 50C that are deflected by the deflection electrode 32 hit the fourth side surface 336, and the electron beam 50B deflected by the deflection electrode 32 hit the fifth side surface 337. In this case, the X-rays 51B are irradiated toward the irradiation window 35. The X-rays 51A and the X-rays 51C are irradiated in a direction different from the position where the irradiation window 35 is provided.

In the case shown in FIG. 4C, the target 33 is arranged such that the electron beam 50A and the electron beam 50B that are deflected by the deflection electrode 32 hit the sixth side surface 338, and the electron beam 50C deflected by the deflection electrode 32 hit the fifth side surface 337. In this case, the X-rays 51C are irradiated toward the irradiation window 35. The X-rays 51A and the X-rays 51B are irradiated in directions different from the position where the irradiation window 35 is provided.

In this variation, the fifth side surface 337 corresponds to the "first surface" and the "fourth surface", and the fourth side surface 336 and the sixth side surface 338 correspond to the "second surface" and the "third surface". By using a configuration in which multiple electron generators are provided, this is also applicable to photon counting.

Furthermore, in order to ensure that the X-rays output from the irradiation window 35 are switched, it is sufficient to adjust the shapes of the side surfaces of the target 33 in accordance with each direction. Moreover, the X-rays 51A and 51B may be generated by providing multiple targets 33 and receiving the electron beams 50A and 50B with different targets 33. Moreover, the electron beams 50A and 50B that advance linearly and the electron beams 50A and 50B that are deflected may be received with different targets 33.

As described above, according to the X-ray CT device of the present embodiments, it is possible to irradiate multiple X-rays from a single X-ray tube 3 by switching between them each time. Therefore, the device does not become complex and the cost is also reduced. Moreover, in the X-ray CT device according to the present embodiments, the electron beams 50A and 50B are constantly irradiated, and the X-rays irradiated from the irradiation window 35 are switched by deflecting these. By using such a configuration, it is possible to electronically control the switching between the X-rays 51A and 51B. As a result, high-rate switching is not able to perform because synchronization is difficult with mechanical switching, but high-rate switching is possible with the X-ray CT device according to the present embodiments. Moreover, it is not necessary to change the voltage between the filament 311 and the target 33 when switching between the X-rays 51A and 51B. Therefore, even when switching between the X-rays 51A and 51B, there is no time lag generated during the period until the change in voltage is completed, and as a result, it is possible to stabilize the output of the X-rays 51A and 51B. As a result, it is possible to prevent image degradation that associated with switching between X-rays.

While certain embodiments have been described, these embodiments have been presented by way of example only, and are not intended to limit the scope of the inventions. Indeed, the novel systems described herein may be embodied in a variety of their forms; furthermore, various omissions, substitutions and changes in the form of the systems described herein may be made without departing from the spirit of the inventions. The accompanying claims and their equivalents are intended to cover such forms or modifications as would fall within the scope and spirit of the inventions.

DESCRIPTION OF SYMBOLS

1: Gantry
2: Rotating ring
3: X-ray tube
31A, 31B: Electron generator
311: Filament
32: Deflection electrode
33: Target
331: Small-diameter surface
332: Large-diameter surface
333: First side surface
334: Second side surface
335: Third side surface
34: Drive member
35: Irradiation window
4: X-ray filter
5: X-ray detector
6: Sliding bed
7: High-voltage generator
8: X-ray controller
9: Gantry/bed controller
10: Controller
11: Deflection controller
12: Data collector
13: Preprocessing unit
14: X-ray projection data memory
15: Reconstruction processing unit
16: Display

The invention claimed is:

1. An X-ray tube comprising:
a first electron generator configured to emit a first electron beam;
a second electron generator configured to emit a second electron beam that is different in energy from the first electron beam;
an X-ray generator including a first surface, the X-ray generator configured to generate a first X-ray upon receipt of the first electron beam, and generate a second X-ray upon receipt of the second electron; and
a deflector configured to selectivety deflect the first electron beam such that the first surface receives the first electron beam or a surface other than the first surface receives the first electron beam,
wherein when the first surface receives the first electron beam, the first X-ray is thereby irradiated toward a predetermined irradiation field, and
when the surface other than the first surface receives the first electron beam, the first X-ray is thereby irradiated in a direction different from direction of the predetermined irradiation field.

2. The X-ray tube according to claim 1, wherein
the X-ray generator further includes a fourth surface,
the deflector is configured to selectively deflect the first electron beam and the second electron beam such that the first surface receives the first electron beam and a surface other than the fourth surface receives the second electron beam, or the surface other than the first surface receives the first electron beam and the fourth surface receives the second electron beam,
when the fourth surface receives the second electron beam, the second X-ray is thereby irradiated toward the predetermined irradiation field, and
when the surface other than the fourth surface receives he second electon beam, the second X-ray is thereby irradiated in a dire n different from dire n of the predetermined irradiation field.

3. The X-ray tube according to claim 1, wherein
when the first surface receives the first electron beam, the first X-ray is thereby irradiated toward the predetermined irradiation field to outside of the X-ray tube, and
when the surface other than the first surface receives the first electron beam, the first X-ray is thereby irradiated in the direction different from the direction of the predetermined irradiation field in the X-ray tube.

4. The X-ray tube according to claim 2, wherein
the deflector is configured to simultaneously switch a direction in which the first electron beam and the second electron beam are transmitted to either a first direction or a second direction that is different from the first direction,
the X-ray generator further includes a second surface and a third surface,
when the first electron beam and the second electron beam are transmitted in the first direction, the first surface receives the first electron beam and thereby the first X-ray is irradiated toward a predetermined irradiation field, and the second surface receives the second electron beam and thereby the second X-ray is irradiated toward a direction different from direction of the predetermined irradiation field, and
when the first electron beam and the second electron beam are transmitted in the second direction, the third surface receives the first electron beam and thereby the first X-ray is irradiated toward a direction different from the direction of the predetermined irradiation field, and the fourth surface receives the second electron beam and thereby the second X-ray is irradiated toward the predetermined irradiation field.

5. The X-ray tube according to claim 4, wherein the deflector comprises a pair of electrodes that are capable of forming an electrical field between each other and are arranged so that the first electron beam and the second electron beam pass through between them, and deflects both the first electron beam and the second electron beam by the electrical field.

6. The X-ray tube according to claim 4, wherein the first surface receives the first electron beam at an incident angle different from an incident angle of the second electron beam transmitted to the fourth surface.

7. The X-ray tube according to claim 6, wherein the deflector comprises a pair of electrodes that are capable of forming an electrical field between each other and are arranged so that the first electron beam and the second electron beam pass through between them, and deflect both the first electron beam and the second electron beam by the electrical field.

8. The X-ray tube according to claim 6, wherein a surface is one of the first surface and the fourth surface and receives an electron beam with high energy and receives the electron beam at a shallower incident angle than an other surface.

9. The X-ray tube according to claim 8, wherein the deflector comprises a pair of electrodes that are capable of forming an electrical field between each other and are arranged so that the first electron beam and the second electron beam pass through between them, and deflects both the first electron beam and the second electron beam by the electrical field.

10. An X-ray CT device comprising:
an X-ray tube with an irradiation window from which X-rays are irradiated toward a subject; and
an X-ray detector configured to detect the X-rays irradiated from the irradiation window,
wherein the X-ray tube includes:
- a first electron generator configured to emit a first electron beam,
- a second electron generator configured to emit a second electron beam that is different in energy from the first electron beam,
- an X-ray generator including a first surface, the X-ray generator configured to generate a first X-ray upon receipt of the first electron beam, and generate a second X-ray upon receipt of the second electron beam, and
- a deflector configured to selectively deflect the first electron beam such that the first surface receives the first electron beam or a surface other than the first surface receives the first electron beam, wherein, when the first surface receives the first electron beam, the first X-ray is thereby irradiated toward a predetermined irradiation field, and
when the surface other than the first surface receives the first electron beam, the first X-ray is thereby irradiated in a direction different from direction of the predetermined irradiation field.

11. The X-ray CT device according to claim 10, wherein
when the first surface receives the first electron beam, the first X-ray is thereby irradiated toward the predetermined irradiation field to outside of the X-ray tube, and
when the surface other than the first surface receives the first electron beam, the first X-ray is thereby irradiated in the direction different from the direction of the predetermined irradiation field in the X-ray tube.

* * * * *